United States Patent
Riskin

(10) Patent No.: US 11,135,334 B2
(45) Date of Patent: Oct. 5, 2021

(54) METHOD OF AIR DISINFECTION AND AN AIR DISINFECTION APPARATUS COMPRISING AN UNIPOLAR CORONA DISCHARGE ZONE AND AN ELECTRICAL FIELD

(71) Applicant: TADIRAN CONSUMER AND TECHNOLOGY PRODUCTS LTD., Petah Tikva (IL)

(72) Inventor: Yefim Riskin, Katzrin (IL)

(73) Assignee: TADIRAN CONSUMER AND TECHNOLOGY PRODUCTS LTD., Petah Tikva (IL)

( * ) Notice: Subject to any disclaimer, the term of this patent is extended or adjusted under 35 U.S.C. 154(b) by 0 days.

(21) Appl. No.: 16/980,365

(22) PCT Filed: Sep. 25, 2019

(86) PCT No.: PCT/IL2019/051058
§ 371 (c)(1),
(2) Date: Sep. 11, 2020

(87) PCT Pub. No.: WO2020/065648
PCT Pub. Date: Apr. 2, 2020

(65) Prior Publication Data
US 2021/0046210 A1 Feb. 18, 2021

(30) Foreign Application Priority Data
Sep. 27, 2018 (IL) .......................................... 262022

(51) Int. Cl.
*A61L 9/22* (2006.01)
*F24F 8/192* (2021.01)
(Continued)

(52) U.S. Cl.
CPC ................ *A61L 9/22* (2013.01); *B01D 53/32* (2013.01); *F24F 8/192* (2021.01); *H01T 19/04* (2013.01);
(Continued)

(58) Field of Classification Search
CPC ... A61L 9/22; F24F 8/192; F24F 8/194; F24F 8/30; B01D 53/32; B01D 2257/91;
(Continued)

(56) References Cited

U.S. PATENT DOCUMENTS 3,417,302 A 12/1968 Lueder et al.
4,673,416 A 6/1987 Sakakibara et al.
(Continued)

OTHER PUBLICATIONS

Written Opinion from the International Preliminary Examining Authority for PCT/IL2019/051058, dated Mar. 30, 2020, 9 pages.
(Continued)

*Primary Examiner* — Xiuyu Tai
(74) *Attorney, Agent, or Firm* — Richard T. Black; Foster Garvey PC

(57) ABSTRACT

In a method and apparatus (10) for air disinfection a unipolar corona discharge zone (26) is formed between an ionizing portion (15) of a first electrode (14) and a non-ionizing second electrode (18) by applying high DC voltage (22', 22") across the first and second electrodes and water molecules in an air flow (25) conveyed through the corona discharge zone are converted to hydrogen peroxide molecules. An electric field (27, 27', 27") is generated across the air flow close to the corona discharge zone for preventing ions escaping from the corona discharge zone into the atmosphere. This allows a higher corona discharge current to be applied than would be permitted if ions were able to escape into the atmosphere, which results in a higher yield of hydrogen peroxide and increases the efficiency of disin-
(Continued)

fection. It also helps to prevent dust from settling on the ionizing portion (15).

9 Claims, 2 Drawing Sheets

(51) Int. Cl.
*B01D 53/32* (2006.01)
*H01T 19/04* (2006.01)
*H01T 23/00* (2006.01)
*F24F 8/30* (2021.01)

(52) U.S. Cl.
CPC .......... *H01T 23/00* (2013.01); *B01D 2257/91* (2013.01); *B01D 2259/818* (2013.01); *F24F 8/194* (2021.01); *F24F 8/30* (2021.01)

(58) Field of Classification Search
CPC ... B01D 2259/818; H01T 19/04; H01T 23/00; B03C 3/011; B03C 3/12; B03C 3/66; B03C 3/60; B03C 3/38; B03C 3/68; B03C 3/41; H05H 1/48; H05H 1/2406; H05H 2245/121; H05H 2001/481; H02M 7/003; Y02A 50/20; B01J 19/08; B01J 19/088; B01J 2219/0809; B01J 2219/0818; B01J 2219/083; B01J 2219/0849; B01J 2219/0898; B01J 2219/0884; B01J 2219/0875

See application file for complete search history.

(56) References Cited

U.S. PATENT DOCUMENTS

| | | |
|---|---|---|
| 9,843,169 B2 | 12/2017 | Riskin et al. |
| 10,020,180 B2 | 7/2018 | Waddell |
| 10,128,075 B2 | 11/2018 | Waddell |
| 2006/0177360 A1* | 8/2006 | On .......................... A61L 9/22 422/186.21 |
| 2012/0269677 A1 | 10/2012 | Zhou et al. |
| 2012/0273342 A1* | 11/2012 | Schenkel ................. G21G 4/02 204/164 |
| 2016/0175803 A1 | 6/2016 | Riskin et al. |

OTHER PUBLICATIONS

International Preliminary Report on Patentability Authority for PCT/IL2019/051058, dated Jun. 26, 2020, 13 pages.
International Search Report and Written Opinion for PCT/IL2019/051058, dated Jan. 24, 2020, 7 pages.

* cited by examiner

Section A-A

METHOD OF AIR DISINFECTION AND AN AIR DISINFECTION APPARATUS COMPRISING AN UNIPOLAR CORONA DISCHARGE ZONE AND AN ELECTRICAL FIELD

FIELD OF THE INVENTION

This invention relates to air disinfection using hydrogen peroxide.

BACKGROUND OF THE INVENTION

Methods for disinfection of air under barometric pressure are known in which hydrogen peroxide ($H_2O_2$) is used as a disinfectant. In known methods $H_2O_2$ is obtained by passing an air flow containing water molecules ($H_2O$) through a corona discharge zone created across two electrodes as a result of high voltage discharge. Water molecules in the air flow are converted into molecules of $H_2O_2$ during interaction with the corona discharge ions.

Bipolar ion generators have become most commonly used for air disinfection of manned premises. Such devices as described, for example, in U.S. Pat. Nos. 9,843,169; 10,020,180 and 10,128,075 and operate based on generating a corona discharge area between ionizing electrodes of opposite polarity through which there is passed either a whole or partial air-flow containing water molecules (humidity). At the outlet of a bipolar ion generator, the air-flow contains concurrently hydrogen peroxide and positive and negative ions captured by the air-flow from the corona discharge area.

A major drawback of bipolar ionizers is their low disinfection efficiency of 99.9 to 99.99%. An efficiency of 99.99% may appear to be high but it means that out of every 10,000 bacteria in the air, one will not be removed by the ionizer. Theoretically, the efficiency could be increased by increasing the corona discharge current, but in practice the corona discharge current is limited by the maximum permitted ion concentration in manned premises set by the relevant Standard to 50,000 ions/$cm^3$. This limitation does not allow for sufficiently high corona discharge to significantly increase the efficiency of disinfection of bacteria, viruses and mold.

Another drawback of disinfectors is the need for periodic cleaning of ionizing electrodes from dust because of the permanent presence of electrically charged dust particles in the air flow as a result of the triboelectric effect, whereby certain materials that rub against a different material become electrically charged after they are separated. When air flows through a disinfector containing an ionizing electrode to which there is applied a high negative voltage, for example, positively charged dust will settle on the electrode because of electrostatic attraction. Taking into account the small surface area of the ionizing electrode tip even a small amount of dust that settles on the tip is liable to hinder or even abort the ionization process.

This brings about the need for periodic cleaning of the electrodes from dust during deployment of the disinfector. Existing methods and devices for automatic periodic cleaning of electrodes from dust are based on the use of actuators such as solenoids or electric wipers which significantly raises the price of such disinfectors.

SUMMARY OF THE INVENTION

It is therefore a principal object of the present invention to provide an improved method and apparatus for disinfecting air, which significantly increases the efficiency compared with bipolar ionizers.

It is a further object of the invention to reduce the need for constant cleaning of the ionizing electrodes.

These objects are realized in accordance with the invention by a method and apparatus for air disinfection having the features of the respective independent claims.

Thus in accordance with one aspect there is provided a method for disinfection of air which includes:

creating a unipolar corona discharge zone between an ionizing portion of a first electrode and a non-ionizing second electrode by applying high DC voltage across the first and second electrodes, and conveying an air flow through the corona discharge zone in order to convert water molecules in the air flow to hydrogen peroxide molecules owing to reaction of the water molecules with corona discharge ions; and generating an electric field across the air flow close to the corona discharge zone for preventing ions escaping from the corona discharge zone into the atmosphere.

This allows a higher corona discharge current to be applied than would be permitted by the relevant Standard if ions were able to escape into the atmosphere, and results in a higher yield of hydrogen peroxide thereby increasing the efficiency of disinfection.

The present invention results in a substantial, more than 10 times, increase in disinfection efficiency, preventing the deposition of dust on the ionizing electrode over the long life of the disinfector, as well as the simplification of the high voltage generator and, therefore, the entire disinfector.

In accordance with one embodiment, the invention employs an ionizing electrode formed of one or more thin-wire shaped electrodes (e.g. needle tips) that operate as an ionizing portion mounted in a non-ionizing metal base, or alternatively a non-conductive base such as plastic to which a suitable electrical contact is attached, that serves as a housing surrounding the thin-wire shaped electrodes.

In a further aspect, auxiliary electrodes are disposed upstream and downstream of the corona discharge zone for generating respective auxiliary electric fields that impede dust found in the air flow from settling onto the ionizing portion of the first electrode.

An apparatus for disinfection of air includes a housing having an air inlet and an air outlet, at least two electrodes, a first of which has an ionizing and a non-ionizing portion, the second electrode being non-ionizing, connection terminals for coupling a unipolar high voltage generator whose high voltage and low voltage outputs are connected to the above electrodes. The first electrode is located at a certain distance from the second electrode so that a corona discharge zone is created between the ionizing portion of the first electrode and the second electrode. Electric fields are generated between the non-ionizing portions of the first electrode and the second electrode mounted close to the corona discharge zone. The ionizing portion of the first electrode is located outside the air flow.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1:
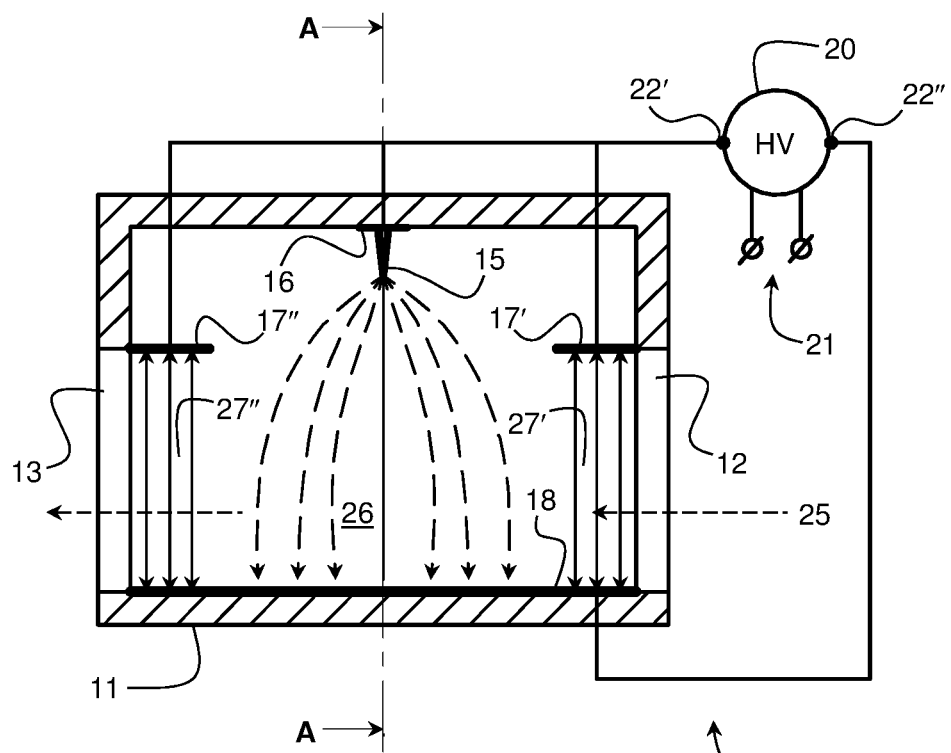
FIG. 1 is a schematic representation of an air disinfector according to the invention.

FIG. 1 shows schematically an apparatus 10 according to an embodiment of the invention comprising a generally hollow housing 11 having an air inlet 12 and an air outlet 13. Mounted within the housing is a first electrode 14 having an ionizing portion 15 mounted in a base 16 having an electrically conductive contact that constitutes a non-ionizing portion and to which preferably there are electrically coupled first and second auxiliary electrodes 17' and 17", which functionally may be considered to be non-ionizing portions of the first electrode 14. A non-ionizing second electrode 18 is also mounted inside the housing displaced from the electrodes 17' and 17" and from the non-ionizing portion 15 of the first electrode 14. The housing 11 as shown is of square cross-section with the air inlet 12 and air outlet 13 formed by apertures in opposed wall surfaces. But it is to be understood that other geometries are possible, wherein the cross-section of the housing is cylindrical or polygonal in shape. In use, air is forced between the air inlet and the outlet. The manner in which this is done depends on the application to which the apparatus is employed. For example, the air flow may be generated by an external fan, which may be part of an air-conditioner. In such case, the apparatus may be mounted inside the air-conditioner or inside an air-conditioning duct through which air is conveyed in known manner.

External to the housing is a unipolar high voltage source 20 having input power terminals 21 for coupling to a suitable power supply. The high voltage source 20 produces high voltage DC across high and low voltage terminals 22', 22" respectively. The high voltage terminal 22' is connected to the first electrode 14, and the low voltage terminal 22" is connected to the second electrode 18.

The air inlet 12 is located in the housing 11 intermediate the first auxiliary electrode 17' and the second electrode 18 while the air outlet 13 is located intermediate the second auxiliary electrode 17" and the second electrode 18. Moreover, the ionizing portion 15 of the first electrode 14 is more displaced from the second electrode 18 than are the first and second auxiliary electrodes 17' and 17", the ionizing portion 15 of the first electrode 14 being located outside the air flow shown as 25.

Figure 2:
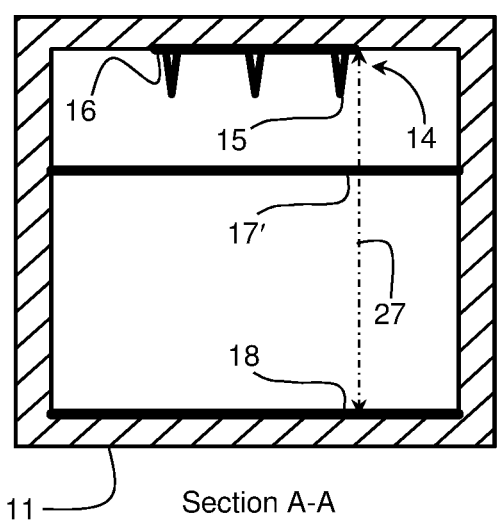
FIG. 2 shows a sectional view along the fine A-A in FIG. 1.

FIG. 2 is a sectional view along the line A-A in FIG. 1 showing the construction of the ionizing portion 15 of the first electrode 14. Thus, the housing 11 is of square or rectangular cross-section with the ionizing portion 15 of the first electrode 14 being mounted centrally in an upper surface of the housing and the second electrode 18 being mounted on its lower surface. The first electrode 14 actually comprises three spaced apart wires or needles mounted in the base 16, although obviously other configurations may be used. The auxiliary electrodes 17' and 17" are planar electrodes mounted on opposed internal wall surfaces of the housing proximate upper edges of the respective air inlet and outlet. While they may be mounted higher, it is preferable that they be mounted closer to the non-ionizing second electrode 18 in order to increase the electric field between the auxiliary electrodes 17', 17" and the second electrode 18. However, they should not be mounted lower than the top of the respective air inlet and outlet so that the complete air flow is constrained to pass through the electric fields.

The direction of the air flow is substantially parallel to the plane of the second electrode 18. The auxiliary electrodes 17', 17" are located above the air inlet 12 and the air outlet 13. Consequently, on entering through the air inlet 12 the complete air stream is constrained to flow through the electric field generated across the auxiliary electrode 17' and the second electrode 18 prior to entering the corona discharge zone 26. Likewise, after exiting the corona discharge zone 26 the air stream is again constrained to flow through the electric field generated across the auxiliary electrode 17" and the second electrode 18 prior to exiting through the air outlet 13.

The apparatus operates as follows. When power is applied to the terminals 21 of the high voltage source 20, high voltage DC is supplied across the first electrode 14 and the second electrode 18 whereby a corona discharge zone 26 is created between the ionizing portion 15 of the first electrode 14 and the second electrode 18. Since the base contact of the first electrode 14 is at the same high DC potential as the ionizing portion 15, there is formed between the base 16 and the second electrode 18, an electric field 27 shown schematically in FIG. 2 by a single dotted line that surrounds the ionizing portion 15. The electric field 27 surrounds the corona discharge zone 26 and operates as an electrostatic filter to prevent charged ions in the corona discharge zone from escaping. Specifically, positive ions in the corona discharge zone will be repelled by the high positive voltage applied to the base 16 and will settle on the second electrode 18. Conversely, negative ions will gravitate toward the base 16. Consequently, very few ions will exit with the air flow through the air outlet 13 and this means that much larger corona discharge currents may be applied than is possible in bipolar ionizers, without exceeding the maximum permitted ion concentration. The efficiency of conversion from water to $H_2O_2$ is a function of the corona discharge current and in an embodiment of the invention reduced to practice the $H_2O_2$ concentration was 10 ppb, well within the maximum FDA limit of 100 ppb, and the power was as little as 0.1 W. This compares with an $H_2O_2$ concentration for bipolar ionizers of comparable power, which is typically 1 ppb.

In addition to the electric field created between the base 16 of the first electrode 14 and the second electrode 18, an electric field 27' is generated between the first auxiliary electrode 17' and the non-ionizing second electrode 18 and an electric field 27" is generated between the second auxiliary electrode 17" and the non-ionizing second electrode 18.

Molecules of $H_2O$ present in the air flow passing through the corona discharge zone 26 are converted into $H_2O_2$ and are removed from the housing 11 of the disinfector 10 through the air outlet 13. The electric fields 27' and 27" do not affect the $H_2O$ and $H_2O_2$ molecules since these molecules are uncharged. On the other hand, charged dust found in the air flow 25 depending on the charge polarity settles onto the surfaces of the first and second auxiliary electrodes 17' and 17" and the second electrode 18 under the action of the electric fields 27' and 27" on the principle of an electrostatic filter.

Dust particles that are not caught by the auxiliary electrodes 17' and 17" reach the corona discharge zone 26 and by force of the corona discharge ions become charged with the same polarity as the voltage applied to the first electrode 14, which prevents the dust from getting close to the ionizing portion 15 of the first electrode 14 because of the electrostatic repulsive force of the same polarity charges. As a result, such dust particles settle on the second electrode 18. Likewise, the electric fields 27' and 27" prevent the influence of any possible electric field external to the disinfector 10, which might otherwise draw the corona discharge ions outside the housing and into the atmosphere. This is prevented by the electric fields 27' and 27" which trap any such ions before they can escape into the atmosphere.

The inventor built a conceptual prototype of a disinfector whose test has approved the achievement of the set goal.

The conceptual prototype has the following specifications:

| 1 | Corona discharge type | Unipolar |
|---|---|---|
| 2 | The high voltage generator type | Unipolar |
| 3 | The distance between the ionizing portion of the first electrode and the second electrode | 14 mm |
| 4 | The distance between the non-ionizing portions of the first electrode and the second electrode | 10 mm |
| 5 | Voltage applied to the first electrode | 5 kV |
| 6 | Air flow velocity | 6 m/sec |
| 7 | Airspace | 27 m$^3$ |
| 8 | Air humidity | 40% |
| 9 | Air temperature | 25° C. |
| 10 | Ozone | 10 ppb |
| 11 | Concentration of H$_2$O$_2$ | 10 ppb |

Disinfection efficacy testing was performed on Methicillin Resistant *Staphylococcus Epidermidis* (MRSE) bacteria in the Aerosol Research and Engineering Laboratories Inc. Olathe Kans., USA. Disinfection efficiency amounted to 99.9999989% in 150 minutes or 99.9996% in 90 minutes. When compared to typical bipolar ionizers having a disinfection efficiency of up to 99.99%, it can be seen that the invention provides an improvement of two orders of magnitude in 90 minutes and three orders of magnitude in 150 minutes, i.e. an efficiency that is up to $10^3$ higher than achieved by good bipolar ionizers.

Prevention of dust settlement on the ionizing portion 15 of the first electrode 14 was tested by measuring the corona discharge current between the electrodes which remained unchanged for six months.

It will be understood that modifications may be made to the construction of the apparatus without departing from the scope of the invention. For example, while the auxiliary electrodes 17', 17" serve primarily to prevent dust from settling on the ionizing portion 15 of the first electrode 14, the electric fields also prevent ions from escaping into the atmosphere. As noted above, the described configuration of the first electrode whereby an electric field is generated close to the corona discharge zone ensures that most ions are retained inside the housing. But in the absence of the base contact, the auxiliary electrodes 17', 17" will also fulfil this function and can therefore also operate as the non-ionizing portion of the first electrode 14. In the apparatus as described the high voltage terminal of the high voltage generator is connected to the ionizing portion of the first electrode with the low voltage terminal being connected to the second electrode, typically at GND. However, it will readily be appreciated that the invention will operate also if these connections are reversed.

It should also be understood that while in the described apparatus the non-ionizing portion of the first electrode is constituted by the base, many other forms of ionizing electrode are known that will operate in similar manner Although it is preferable that the second electrode be closer to the auxiliary electrodes than to the ionizing electrode, the auxiliary electrodes can be located so as to completely surround the corona discharge. Although they will then be less effective at trapping charged dust in the air, they will then prevent ions in the corona discharge from escaping into the atmosphere. In such a configuration, the auxiliary electrodes serve the same function as the non-ionizing portion of the first electrode of the described embodiment. Therefore, within the scope of the invention and the appended claims, the term "non-ionizing portion" of the first electrode also includes the possibility that this is constituted by one or more auxiliary electrodes. These may then simultaneously serve the dual function of retaining ions in the corona discharge zone within the housing as well as impeding dust from settling on the ionizing portion of the first electrode.

Figure 3:
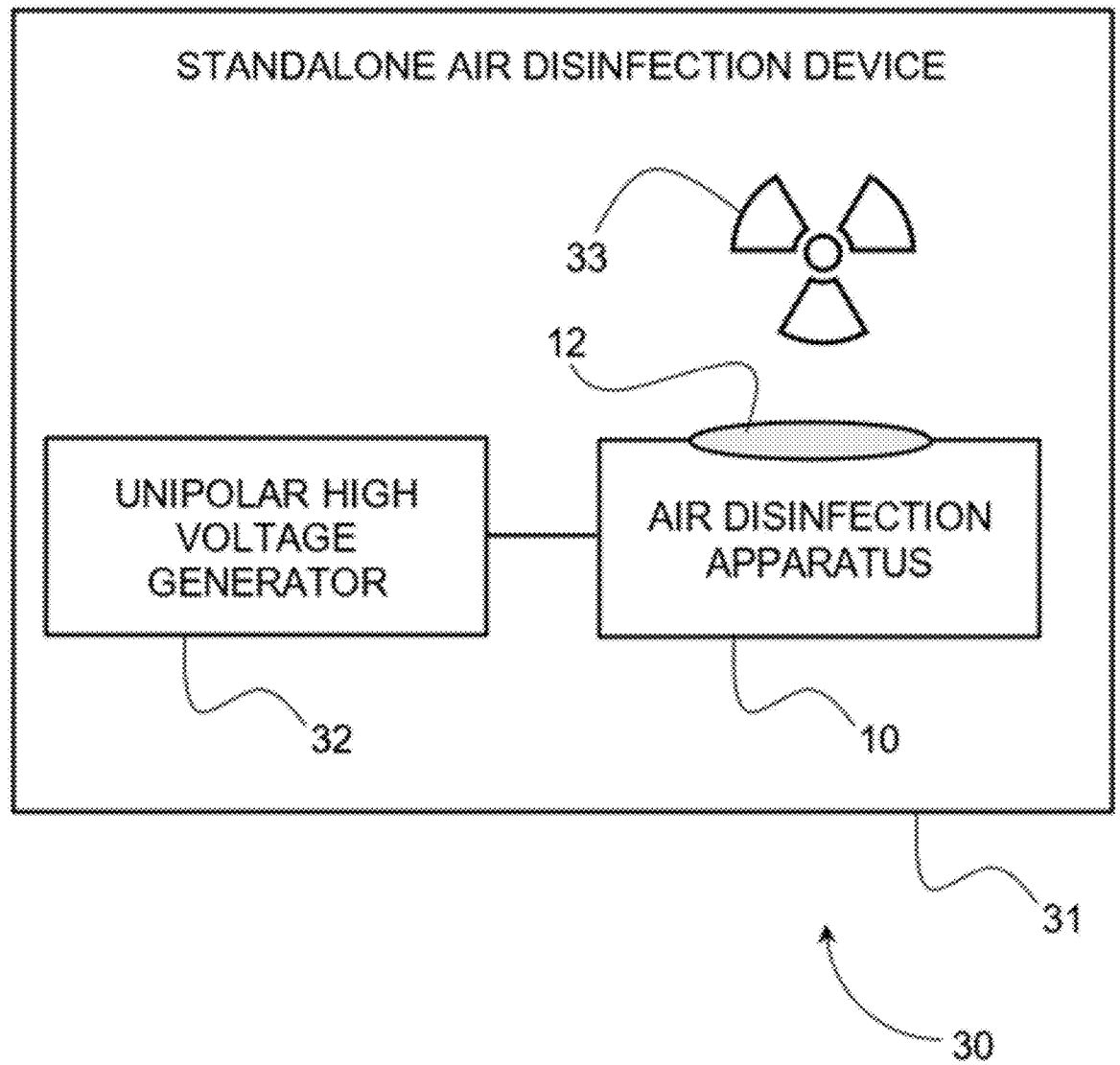
FIG. 3 is a schematic representation of a standalone air disinfection device according to the invention.

It will also be appreciated that the apparatus has been described without specific reference to the manner in which the air flow is generated. FIG. 3 shows schematically a standalone device 30 that can be enclosed inside a casing 31 that houses the air disinfection aparatus 10 having an air inlet 12 as described above and also contains a unipolar high voltage generator 32 and a fan 33, which creates the air stream. Such a standalone device can be deployed in domestic premises such as the home or may be deployed in vehicles, both private and public such as buses, airplanes and so on. In other uses, the apparatus can be mounted inside an existing air stream such as an air-conditioner duct or an air-conditioner unit in which case the fan can be omitted.

The invention claimed is:

1. A method for disinfection of air which includes:
creating a unipolar corona discharge zone between an ionizing portion of a first electrode and a non-ionizing second electrode by applying high DC voltage across the first and second electrodes, said high DC voltage being of sufficient voltage to create a corona discharge zone between the ionizing portion of the first electrode and the second electrode;
conveying an air flow through the corona discharge zone in order to convert water molecules in the air flow to hydrogen peroxide molecules owing to reaction of the water molecules with corona discharge ions;
generating respective auxiliary electric fields between the second electrode and respective auxiliary electrodes disposed respectively upstream and downstream of the air flow on opposite sides of corona discharge zone so as generate respective DC electric fields on oppposite sides of the corona discharge zone, for preventing ions escaping from the corona discharge zone into the atmosphere and for impeding dust found in the air flow from settling onto the ionizing portion of the first electrode.

2. The method according to claim 1, wherein the ionizing portion of the first electrode is mounted in a base having an electrically conductive contact that constitutes a non-ionizing portion.

3. The method according to claim 1, including deploying larger auxiliary electric fields relative to the electric field between the ionizing portion of the first electrode and the second electrode.

4. The method according to claim 3, wherein the auxiliary electrodes are disposed a first height, $h_1$; from the second electrode and the ionizing portion of the first electrode is disposed a second height, $h_2$, from the second electrode and $h_1$ is smaller than $h_2$.

5. An apparatus for air disinfection comprising:
a hollow housing having an air inlet and an air outlet for conveying air therethrough,
a first electrode mounted inside the housing and having an ionizing portion and a non-ionizing portion,
the first electrode being mounted intermediate the air inlet and the air outlet;
a non-ionizing second electrode mounted inside the housing facing the first electrode, terminals electrically connected to the first and second electrodes for coupling thereto high and low voltage outputs of a DC high voltage generator of sufficient voltage to create a corona discharge zone across the air flow between the ionizing portion of the first electrode and the second electrode, and first and second auxiliary electrodes disposed inside the housing toward the end inlet and the outlet, respectively for generating respective auxiliary DC electric fields that prevent ions escaping from the corona discharge zone into the atmosphere and impede dust found in the air flow from settling onto the ionizing portion of the first electrode.

6. The apparatus according to claim 5, wherein the ionizing portion of the first electrode is mounted in a base having an electrically conductive contact that constitutes the portion.

7. The apparatus according to claim 5, wherein the auxiliary electrodes are disposed a first height, $h_1$, from the second electrode and the ionizing portion of the first electrode is disposed a second height, $h_2$, from the second electrode and $h_1$ is smaller than $h_2$.

8. A standalone air disinfection device having a casing containing the apparatus according to claim 5, and further comprising within the casing a unipolar high voltage generator.

9. The standalone air disinfection device according to claim 8, further comprising within the casing a fan external to the air inlet for creating the air flow.

* * * * *